US008603277B2

(12) United States Patent
Paldey et al.

(10) Patent No.: US 8,603,277 B2
(45) Date of Patent: Dec. 10, 2013

(54) METHOD FOR ASSEMBLING DISPOSABLE ABSORBENT ARTICLES WITH AN EMBOSSED TOPSHEET

(75) Inventors: Sohini Paldey, Cincinnati, OH (US); Darrell Ian Brown, Mason, OH (US); Andreas Josef Dreher, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 279 days.

(21) Appl. No.: 13/047,029

(22) Filed: Mar. 14, 2011

(65) Prior Publication Data

US 2012/0234475 A1    Sep. 20, 2012

(51) Int. Cl.
*A61F 13/539*    (2006.01)

(52) U.S. Cl.
USPC ................ 156/209; 604/385.01; 604/385.23

(58) Field of Classification Search
None
See application file for complete search history.

(56) References Cited

U.S. PATENT DOCUMENTS

| | | | |
|---|---|---|---|
| 3,860,003 A | 1/1975 | Buell et al. | |
| 4,610,678 A | 9/1986 | Weisman et al. | |
| 4,834,735 A | 5/1989 | Alemany et al. | |
| 4,888,231 A | 12/1989 | Angstadt | |
| 4,940,464 A | 7/1990 | Van Gompel et al. | |
| 5,037,416 A | 8/1991 | Allen et al. | |
| 5,092,861 A | 3/1992 | Nomura et al. | |
| 5,137,537 A | 8/1992 | Herron et al. | |
| 5,151,092 A | 9/1992 | Buell et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,387,207 A | 2/1995 | Dyer et al. | |
| 5,397,316 A | 3/1995 | LaVon et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,702,551 A | 12/1997 | Huber et al. | |
| 5,897,545 A | 4/1999 | Kline et al. | |

(Continued)

FOREIGN PATENT DOCUMENTS

| | | |
|---|---|---|
| EP | 0 149 880 A2 | 7/1985 |
| EP | 1 348 413 A1 | 10/2003 |

(Continued)

OTHER PUBLICATIONS

12029 PCT International Search Report, mailed May 22, 2012, 12 pages.

(Continued)

*Primary Examiner* — Barbara J Musser
(74) *Attorney, Agent, or Firm* — Charles R. Matson

(57) ABSTRACT

Aspects of the methods herein relate to the fabrication of absorbent articles wherein a continuous topsheet web is advanced in a machine direction. A liquid acquisition layer and an absorbent core are combined with the continuous topsheet web. The combined continuous topsheet web, liquid acquisition layer, and absorbent core advance through the embossing nip to emboss a pattern in the continuous topsheet web. As the combined continuous topsheet web, liquid acquisition layer, and absorbent core advance through the embossing nip, the rotating patterned embossing roll contacts the continuous topsheet web. And the rotating anvil roll contacts the absorbent core. By advancing the topsheet together with the acquisition layer and absorbent core through the embossing nip, a relatively deep pattern can be embossed into the topsheet than otherwise might be possible when embossing relatively thin topsheet web materials.

12 Claims, 14 Drawing Sheets

(56) References Cited

U.S. PATENT DOCUMENTS

| | | |
|---|---|---|
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,443,936 B1 * | 9/2002 | Hamilton et al. ............ 604/387 |
| 6,620,276 B1 | 9/2003 | Kuntze et al. |
| 6,645,569 B2 | 11/2003 | Cramer et al. |
| 6,811,019 B2 | 11/2004 | Christian et al. |
| 6,863,933 B2 | 3/2005 | Cramer et al. |
| 7,078,583 B2 | 7/2006 | Kudo et al. |
| 7,112,621 B2 | 9/2006 | Rohrbaugh et al. |
| 7,587,966 B2 | 9/2009 | Nakakado et al. |
| 2002/0120249 A1 | 8/2002 | Wada et al. |
| 2003/0105190 A1 | 6/2003 | Diehl et al. |
| 2003/0148684 A1 | 8/2003 | Cramer et al. |
| 2003/0233082 A1 | 12/2003 | Kline et al. |
| 2004/0158212 A1 | 8/2004 | Ponomarenko et al. |
| 2005/0008839 A1 | 1/2005 | Cramer et al. |
| 2005/0159720 A1 | 7/2005 | Gentilcore et al. |
| 2006/0122572 A1 | 6/2006 | Suarez |
| 2008/0021426 A1 | 1/2008 | Nakagawa et al. |
| 2008/0039814 A1 | 2/2008 | Jean |
| 2008/0132864 A1 | 6/2008 | Lawson et al. |
| 2009/0247977 A1 | 10/2009 | Takeuchi et al. |
| 2010/0036339 A1 | 2/2010 | Hammons et al. |
| 2010/0036347 A1 | 2/2010 | Hammons et al. |
| 2010/0036349 A1 | 2/2010 | Hammons et al. |

FOREIGN PATENT DOCUMENTS

| | | |
|---|---|---|
| EP | 1 842 512 A1 | 10/2007 |
| WO | WO 95/16746 | 6/1995 |
| WO | WO 01/17475 A1 | 3/2001 |
| WO | WO 02/064877 | 8/2002 |

OTHER PUBLICATIONS

U.S. Appl. No. 13/047,133, filed Mar. 14, 2011, Sohini Paldey.

U.S. Appl. No. 13/047,133, filed Mar. 14, 2011—Office Action mailed May 3, 2013, (9 pages).

* cited by examiner

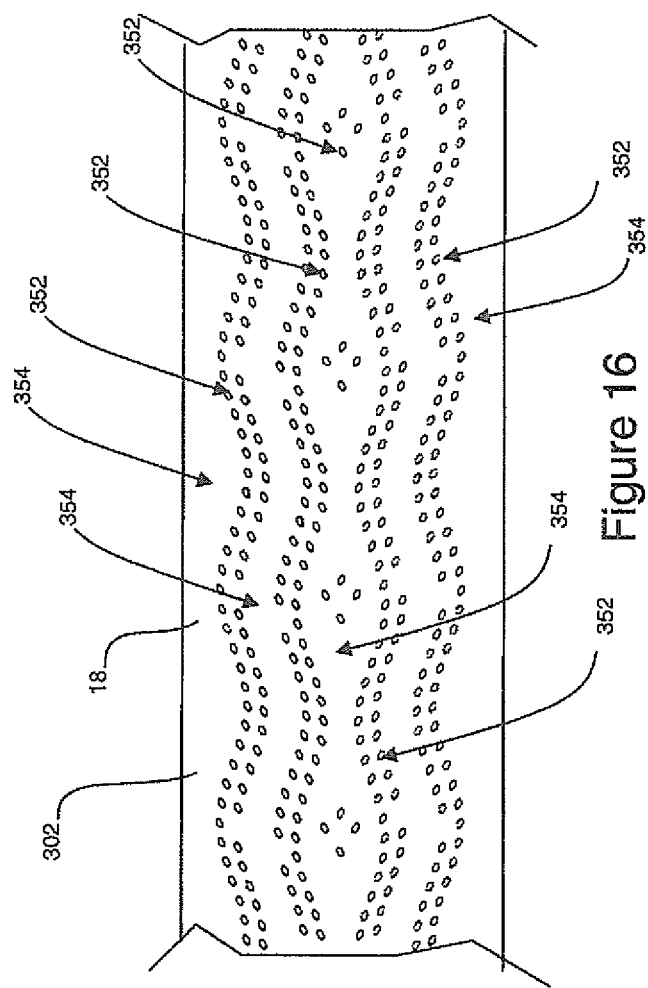

METHOD FOR ASSEMBLING DISPOSABLE ABSORBENT ARTICLES WITH AN EMBOSSED TOPSHEET

FIELD OF THE INVENTION

The present disclosure relates to methods for manufacturing disposable absorbent articles having a topsheet, backsheet, acquisition layer, and absorbent core, and more particularly, to methods for embossing a topsheet web while combined with an acquisition layer and absorbent core.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, acquisition layers, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

The topsheets and/or backsheets of absorbent articles are sometimes constructed from nonwoven webs, plastic films, and/or laminates thereof. In addition, the topsheets and backsheets of such absorbent articles may function to absorb and/or contain the discharged materials and also to isolate bodily exudates from the wearer's skin and from the wearer's garments and bed clothing. In some instances, these substrates are substantially smooth, flat and aesthetically unappealing. Efforts have been made to modify these substrates in order to provide them with a particular appearance. For example, such substrates may be modified to exhibit a softer, quilted, and/or cloth-like appearance. In some examples, these substrates may be modified to include an interior design signal to communicate to a caregiver that a relatively thin absorbent article provides adequate absorbency. As such, nonwoven fabrics and/or plastic films are sometimes modified to provide a physical or actual three-dimensional pattern. Non-limiting examples of known methods which provide an actual three-dimensional appearance to a substrate include embossing. In some configurations, the topsheet is embossed before being combined with other components. However, it may be difficult to emboss a relatively deep pattern and/or impart a very definitive three-dimensional pattern into relatively thin topsheet material. Improved methods for topsheet embossing during absorbent article assembly may be desirable.

SUMMARY OF THE INVENTION

The present disclosure relates to methods for making absorbent articles with embossed topsheets. Aspects of the methods discussed herein relate to the fabrication of absorbent articles wherein a continuous topsheet web having a first surface and an opposing second surface is advanced in a machine direction. A liquid acquisition layer and an absorbent core are combined with the continuous topsheet web. The combined continuous topsheet web, liquid acquisition layer, and absorbent core through the embossing nip to emboss a pattern in the continuous topsheet web. The embossing nip may be defined between a rotating patterned embossing roll and a rotating anvil roll. As the combined continuous topsheet web, liquid acquisition layer, and absorbent core advance through the embossing nip, the rotating patterned embossing roll contacts the continuous topsheet web. And the rotating anvil roll contacts the absorbent core. By advancing the topsheet together with the acquisition layer and absorbent core through the embossing nip, a relatively deep pattern can be embossed into the topsheet than otherwise might be possible when embossing relatively thin topsheet web materials.

In one form, a process may be adapted for assembling disposable absorbent articles, wherein each absorbent article includes a chassis having a first waist region longitudinally opposed to a second waist region, and having a longitudinal axis and a lateral axis, the chassis comprising: a topsheet, a backsheet, and a liquid acquisition layer and a substantially cellulose free absorbent core disposed between the topsheet and the backsheet. The process may include the steps of: advancing a continuous topsheet web having a first surface and an opposing second surface in a machine direction; combining a liquid acquisition layer with the continuous topsheet web, wherein the liquid acquisition layer includes a first surface and an opposing second surface, and wherein the first surface of the liquid acquisition layer is positioned in a facing relationship with the second surface of the continuous topsheet web; combining an absorbent core with the liquid acquisition layer, wherein the absorbent core includes a first surface and an opposing second surface, and wherein the first surface of the absorbent core is positioned in a facing relationship with the second surface of the liquid acquisition layer; providing an embossing nip between a rotating patterned embossing roll and a rotating anvil roll; and embossing a pattern in the continuous topsheet web by advancing the combined continuous topsheet web, liquid acquisition layer, and absorbent core through the embossing nip, wherein the rotating patterned embossing roll contacts the first surface of the continuous topsheet web, and wherein the rotating anvil roll contacts the second surface of the absorbent core.

In another form, a process may be adapted for assembling disposable absorbent articles, wherein each absorbent article comprising a chassis having a first waist region longitudinally opposed to a second waist region, and having a longitudinal axis and a lateral axis, the chassis comprising: a topsheet, a backsheet, and a liquid acquisition layer and a substantially cellulose free absorbent core disposed between the topsheet and the backsheet. The process may include the steps of: advancing a continuous topsheet web having a first surface and an opposing second surface in a machine direction; combining a liquid acquisition layer with the continuous topsheet web, wherein the liquid acquisition layer includes a first surface and an opposing second surface, and wherein the first surface of the liquid acquisition layer is positioned in a facing relationship with the second surface of the continuous topsheet web; combining an absorbent core with the liquid acquisition layer, wherein the absorbent core includes a first surface and an opposing second surface, and wherein the first surface of the absorbent core is positioned in a facing relationship with the second surface of the liquid acquisition layer; providing an embossing nip between a rotating embossing roll and a rotating anvil roll, the embossing roll comprising an embossing element; and creating indented regions in the continuous topsheet web by advancing the combined continuous topsheet web, liquid acquisition layer, and absorbent core through the embossing nip, wherein the embossing element contacts the first surface of the continuous topsheet web, and wherein the rotating anvil roll contacts the second surface of the absorbent core.

BRIEF DESCRIPTION OF THE DRAWINGS

FIG. 16 is a plan view of a topsheet web including a pattern of discrete embossments, such as taken along line 16-16 in FIG. 14.

DETAILED DESCRIPTION OF THE INVENTION

The following term explanations may be useful in understanding the present disclosure:

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure that may be disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
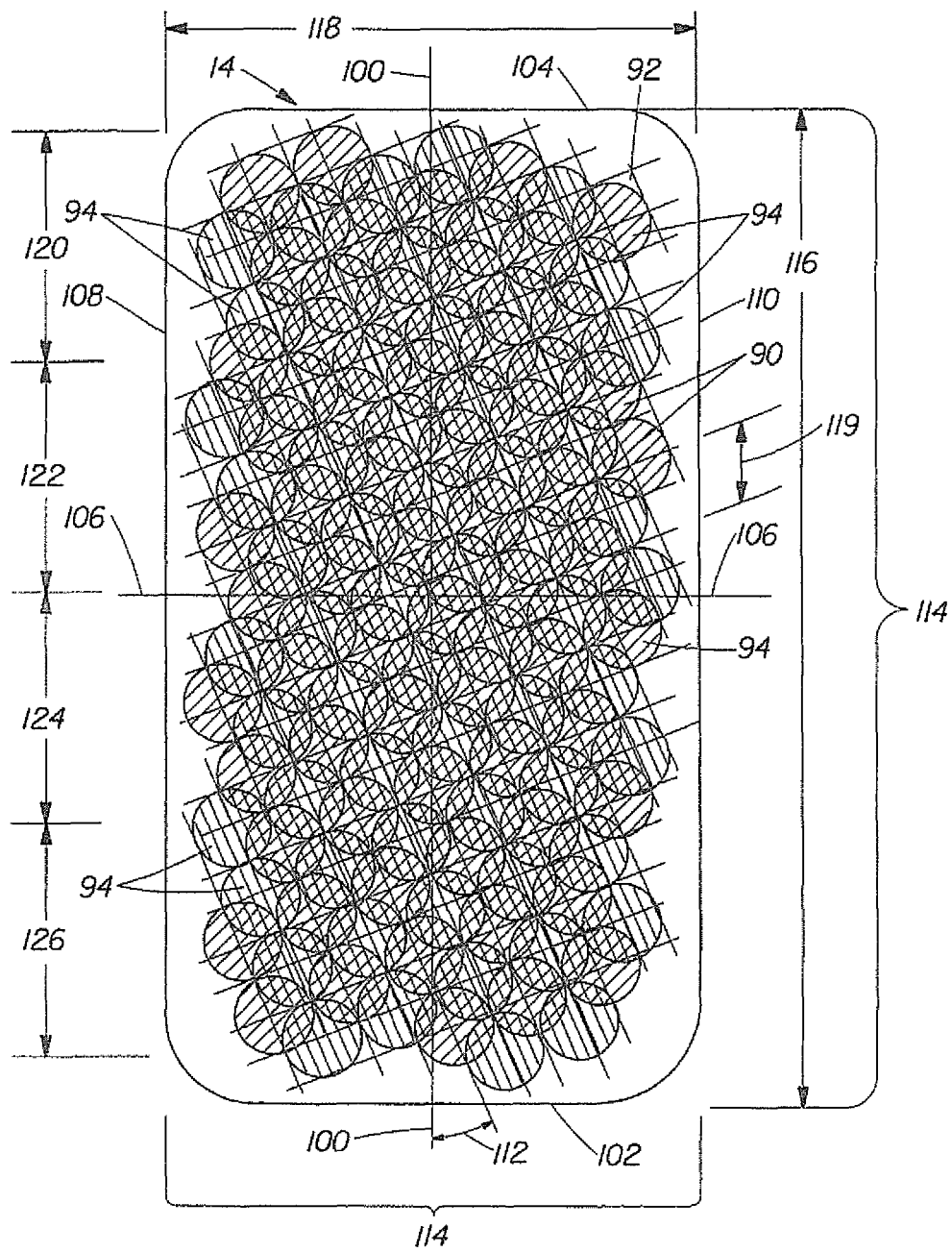
FIG. 8 is a plan view of the absorbent core illustrated in FIGS. 7a and 7b.

"Absorbent particulate polymer material area" as used herein refers to the area of the core wherein the first substrate 64 and second substrate 72 are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate 64 and second substrate 72.

"Airfelt" is used herein to refer to comminuted wood pulp, which is a form of cellulosic fiber.

The term "body facing surface" and "body facing side" refer to surfaces of absorbent articles and/or components thereof which face a wearer's body when the absorbent articles are worn, and the term "garment facing surface" and "garment facing side" refer to surfaces of absorbent articles and/or components thereof that face away from a wearer's body when the absorbent articles are worn. Absorbent articles and components thereof, including the topsheet, backsheet, absorbent core, and any individual materials of their components, have a body facing surface and/or side and a garment facing surface and/or side.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes a "pant" which is defined below.

"Fiber" and "filament" are used interchangeably.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "machine direction" (MD) is used herein to refer to the direction of material flow through a process. In addition, relative placement and movement of material can be described as flowing in the machine direction through a process from upstream in the process to downstream in the process. The term "cross direction" (CD) is used herein to refer to a direction that is generally perpendicular to the machine direction.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present disclosure forms a fibrous network over the superabsorbent material.

"Thickness" and "caliper" are used herein interchangeably.

The present disclosure relates to methods for manufacturing absorbent articles, and in particular, methods for making absorbent articles with embossed topsheets. As discussed in more detail below, absorbent articles, such as diapers may include a chassis having a first waist region longitudinally opposed to a second waist region, and having a longitudinal axis and a lateral axis, the chassis comprising: a topsheet, a backsheet, and a liquid acquisition layer and a substantially cellulose free absorbent core disposed between the topsheet and the backsheet. Aspects of the methods according to the present disclosure relate to the fabrication of absorbent articles wherein a continuous topsheet web having a first surface and an opposing second surface is advanced in a machine direction. A liquid acquisition layer and an absorbent core are combined with the continuous topsheet web. The combined continuous topsheet web, liquid acquisition layer, and absorbent core advance through the embossing nip to emboss a pattern in the continuous topsheet web. As discussed in more detail below, the embossing nip may be defined between a rotating patterned embossing roll and a rotating anvil roll. As the combined continuous topsheet web, liquid acquisition layer, and absorbent core advance through the embossing nip, the rotating patterned embossing roll contacts the continuous topsheet web. And the rotating anvil roll contacts the second surface of the absorbent core. By advancing the topsheet together with the acquisition layer and absorbent core through the embossing nip, a relatively deeper pattern can be embossed into the topsheet than otherwise might be possible when embossing relatively thin topsheet web materials.

The following provides a general description of various types of absorbent articles that may be produced with the methods and apparatuses disclosed herein to help provide additional context to the subsequent discussion of the process embodiments.

Figure 1:
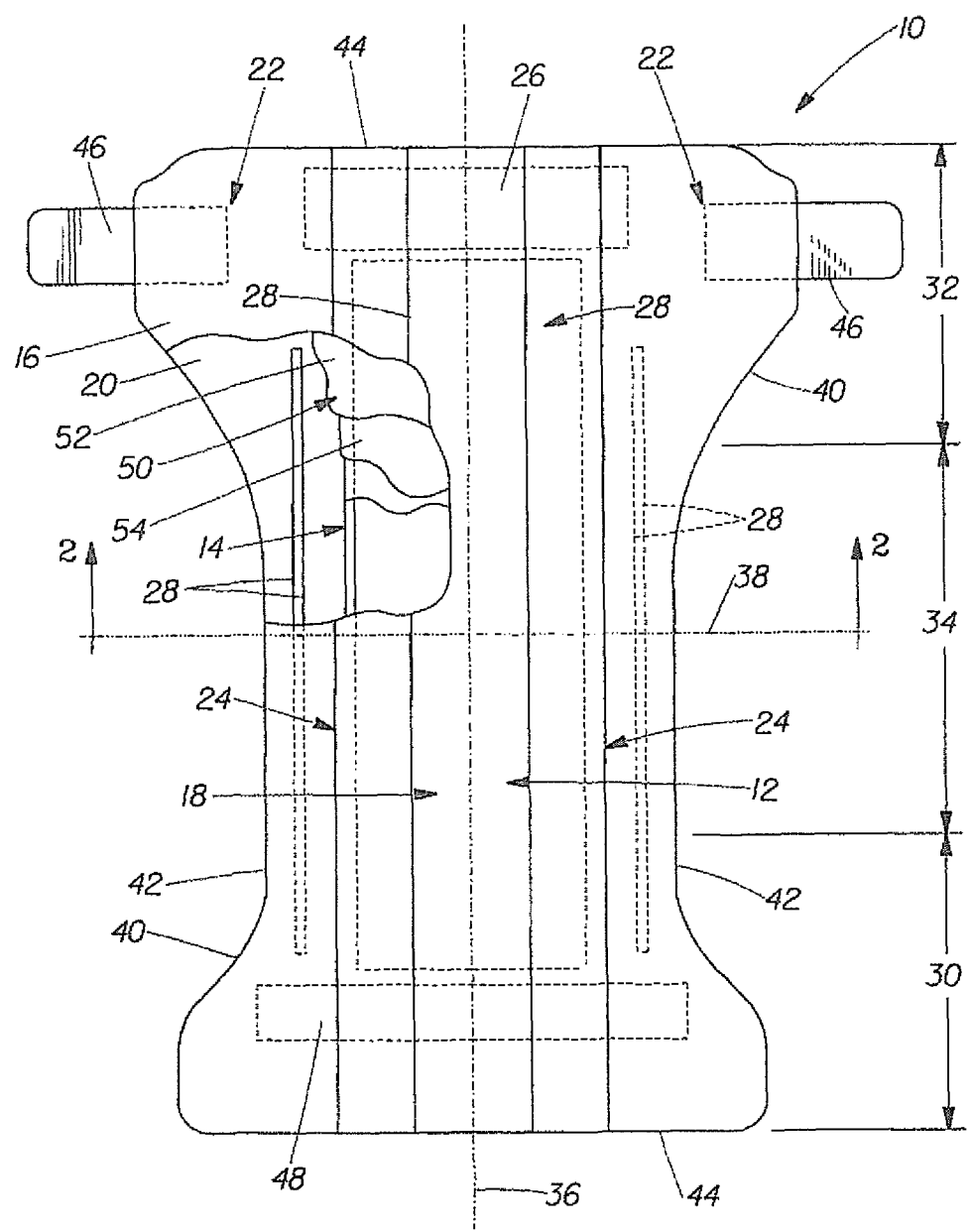
FIG. 1 is a plan view of a diaper.

FIG. 1 is a plan view of a diaper 10 is shown in a flat out, uncontracted state (i.e., without elastic induced contraction)

and with portions of the diaper 10 are cut away to more clearly show the underlying structure of the diaper 10. A portion of the diaper 10 that contacts a wearer is facing the viewer in FIG. 1. The diaper 10 generally may include a chassis 12 and an absorbent core 14 disposed in the chassis.

The chassis 12 of the diaper 10 in FIG. 1 may include an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each include elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with a longitudinal axis 36 and a transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, as well as containment and aesthetic characteristics. Such additional features are described, for example, in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist opening. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

In some embodiments, the diaper 10 may be provided with a re-closable fastening system or may alternatively be provided in the form of a pant-type diaper. When the absorbent article is a diaper, it may include a re-closable fastening system joined to the chassis for securing the diaper to a wearer. When the absorbent article is a pant-type diaper, the article may include at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In some embodiments, the materials making up the fastening device may be flexible. The flexibility may allow the fastening system to conform to the shape of the body and thus, reduce the likelihood that the fastening system will irritate or injure the wearer's skin.

It is to be appreciated that the topsheet 18, the backsheet 20, and the absorbent core 14 may be assembled in a variety of configurations, such as for example as described generally in U.S. Pat. Nos. 5,554,145; 5,569,234; and 6,004,306.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. Nos. 5,037,416 and 5,269,775.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096.

Figure 2:
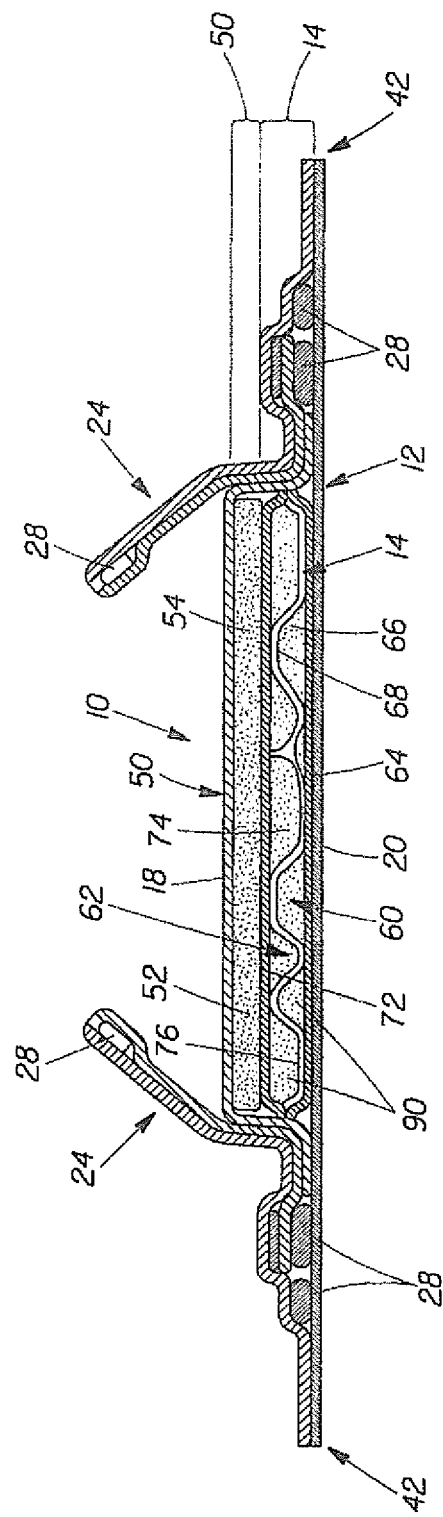
FIG. 2 is a cross sectional view of the diaper shown in FIG. 1 taken along the sectional line 2-2 of FIG. 1.

FIG. 2 is a cross sectional view of the diaper in FIG. 1 taken along the line 2-2. As shown in FIG. 2, the topsheet 18 may define an inner, body facing surface, and the backsheet may define an outer, garment facing surface of the diaper 10. And the absorbent core 14 may be positioned between the topsheet and the backsheet. The diaper 10 may also include an acquisition system 50 disposed between the liquid permeable topsheet 18 and a wearer facing side of the absorbent core 14. The acquisition system 50 may be in direct contact with the absorbent core. The acquisition system 50 (also referred to herein as a liquid acquisition layer 50) may comprise a single layer or multiple layers, such as an upper acquisition layer 52 (also referred to herein as a first acquisition layer 52) facing towards the wearer's skin and a lower acquisition layer 54 (also referred to herein as a second acquisition layer 54) facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In some embodiments, the acquisition system 50 may include chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In some embodiments, polyacrylic acids may be used. Further, according to some embodiments, the cross-linked cellulosic fibers have a water retention value of about 25 to about 60, or about 28 to about 50, or about 30 to about 45. A method for determining water retention value is disclosed in U.S. Pat. No. 5,137,537. In some embodiments, the cross-linked cellulosic fibers may be crimped, twisted, or curled, or a combination thereof including crimped, twisted, and curled.

In some embodiments, one or both of the upper acquisition layer 52 and lower acquisition layer 54 may include a nonwoven, which may be hydrophilic. Further, according to some embodiments, one or both of the upper acquisition layer 52 and lower acquisition layer 54 may comprise the chemically cross-linked cellulosic fibers, which may or may not form part of a nonwoven material. In some embodiments, the upper acquisition layer 52 may comprise a nonwoven, without the cross-linked cellulosic fibers, and the lower acquisition layer 54 may comprise the chemically cross-linked cellulosic fibers. Further, in some embodiments, the lower acquisition layer 54 may comprise the chemically cross-linked cellulosic fibers mixed with other fibers such as natural or synthetic polymeric fibers. According to some embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. In some embodiments, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to some embodiments, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

For example, in some embodiments, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable nonwoven materials for the upper acquisition layer 52 and lower acquisition layer 54 include, but are not limited to SMS material, comprising a spunbonded, a meltblown and a further spunbonded layer. In certain embodiments, permanently hydrophilic nonwovens, and in particular, nonwovens with durably hydrophilic coatings are desirable. Another suitable embodiment comprises a SMMS-structure. In certain embodiments, the nonwovens are porous.

In certain embodiments, suitable nonwoven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in U.S. Pat. No. 7,112,621 and in PCT Publication No. WO 02/064877.

Nanoparticles may have a largest dimension of below 750 nm. Nanoparticles with sizes ranging from 2 to 750 nm may be economically produced. Some nanoparticles can be easily dispersed in water solution to enable coating application onto the nonwoven, form transparent coatings, and the coatings applied from water solutions are may be sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated nonwoven is that disclosed in the U.S. Patent Publication No. 20040158212A1.

Other nonwovens are described in U.S. Pat. Nos. 6,645,569; 6,863,933; and 7,112,621 as well as U.S. Patent Publication Nos. 20030148684A1 and 20050008839A1.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic nonwovens may be used in other parts of an absorbent article. For example, topsheets and absorbent core layers comprising permanently hydrophilic nonwovens as described above can be used.

According to some embodiments, the upper acquisition layer 52 may include a material that provides recovery when external pressure is applied and removed. Further, according to some embodiments, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, embodiments may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to some embodiments, the fibers may include bi-component fibers, which are individual fibers each comprising different materials, usually a first and a second polymeric material.

The upper acquisition layer 52 may be stabilized by a latex binder, for example a styrene-butadiene latex binder (SB latex), in a certain embodiment. Processes for obtaining such lattices are known, for example, from EP Patent Publication No. EP0149880A2 and U.S. Patent Publication No. 20030105190. In some embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
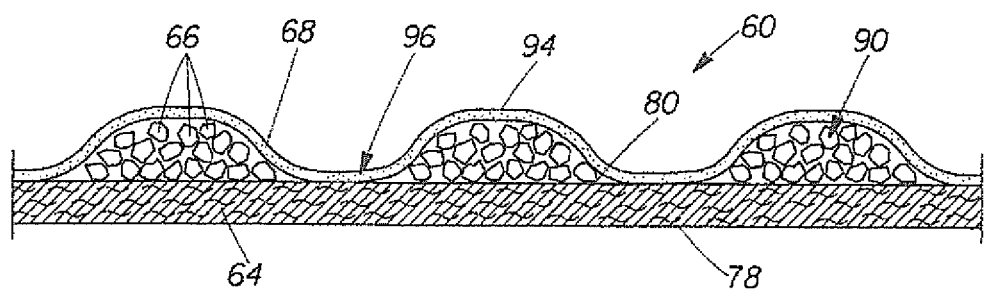
FIG. 3 is a partial cross sectional view of an absorbent core layer.

The absorbent core 14, such as shown in FIGS. 1-8 may be disposed between the topsheet 18 and the backsheet 20 and may include two layers, a first absorbent layer 60 and a second absorbent layer 62. As shown in FIG. 3, the first absorbent layer 60 of the absorbent core 14 may include a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

As shown in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. The substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

In some embodiments, the substrates 64 and 72 of the first and second absorbent layers 60 and 62 may be a nonwoven material, such as those nonwoven materials described above. In some embodiments, the nonwovens are porous and may have a pore size of about 32 microns.

As shown in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
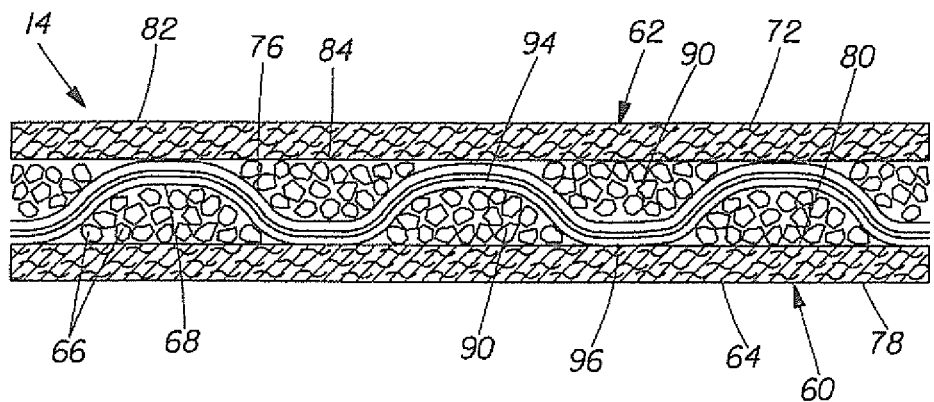
FIG. 7a is a partial sectional view of an absorbent core comprising a combination of the first and second absorbent core layers illustrated in FIGS. 5 and 6.
Figure 7B:
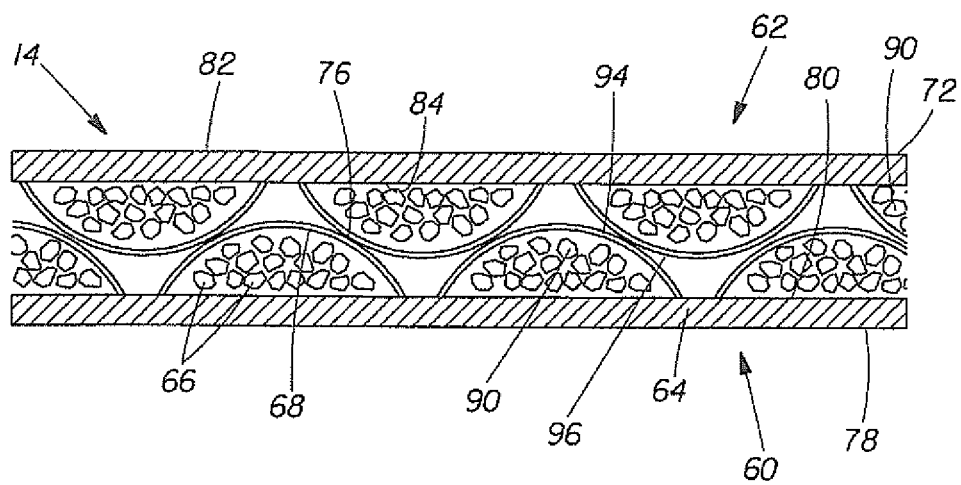
FIG. 7b is a partial sectional view of an absorbent core comprising a combination of the first and second absorbent core layers illustrated in FIGS. 5 and 6.

As shown in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In some embodiments, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In some embodiments, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In some embodiments, such as shown in FIG. 8, the amount of absorbent particulate polymer material 66 and 74 may vary along the length 116 of the grid pattern 92. The grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core 14 consists essentially of the first and second substrates 64 and 72, the absorbent particulate polymer material 66 and 74, and the thermoplastic adhesive composition 68 and 76. In some embodiments, the absorbent core 14 may be substantially cellulose free.

In some embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a some embodiments, the first and the second square are centered about the longitudinal axis.

The absorbent particulate polymer material area may have a relatively narrow width in the crotch area of the absorbent article for increased wearing comfort. Hence, the absorbent particulate polymer material area may have a width as measured along a transverse line which is positioned at equal distance to the front edge and the rear edge of the absorbent article, which is less than about 100 mm, 90 mm, 80 mm, 70 mm, 60 mm or even less than about 50 mm.

It some absorbent articles, such as diapers, liquid discharge from the wearer may occur predominately in the front half of the diaper. The front half of the absorbent core 14 may therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like. Exemplary absorbent structures for use as the absorbent assemblies are described in U.S. Pat. Nos. 4,610,678; 4,834,735; 4,888,231; 5,260,345; 5,387,207; 5,397,316; and 5,625,222.

Figure 4:
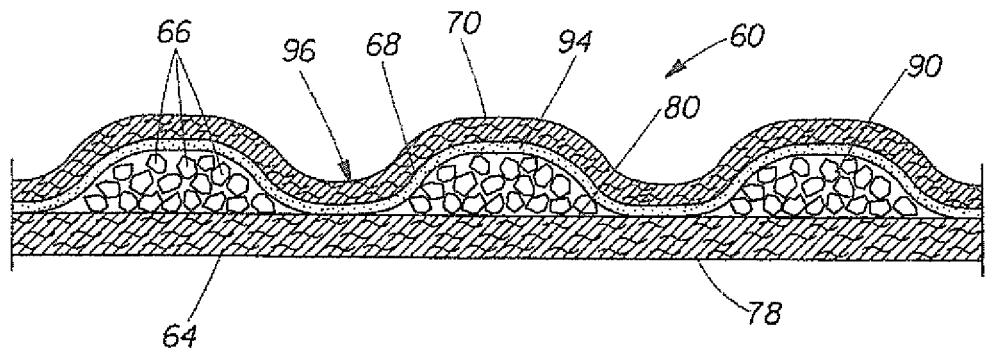
FIG. 4 is a partial cross sectional view of an absorbent core layer.

The thermoplastic adhesive material 68 and 76 may serve to cover and at least partially immobilize the absorbent particulate polymer material 66 and 74. In some embodiments, the thermoplastic adhesive material 68 and 76 can be disposed essentially uniformly within the absorbent particulate polymer material 66 and 74, between the polymers. In some embodiments, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure wherein the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer may have a molecular weight (Mw) of more than 10,000 and a glass transition temperature (Tg) usually below room temperature or $-6°\,C.>Tg<16°\,C.$ In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin may have a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers may have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other nonwoven layer, such layers may be pre-treated with an auxiliary adhesive.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 in various ways. For example, in some embodiments, the auxiliary glue may be applied in about 0.5 to about 1 mm wide slots spaced about 0.5 to about 2 mm apart.

The cover layer 70 shown in FIG. 4 may include the same material as the substrates 64 and 72, or may include a different material. In certain embodiments, the materials of the cover layer 70 are the nonwoven materials, such as the materials described above as useful for the substrates 64 and 72.

Figure 9:
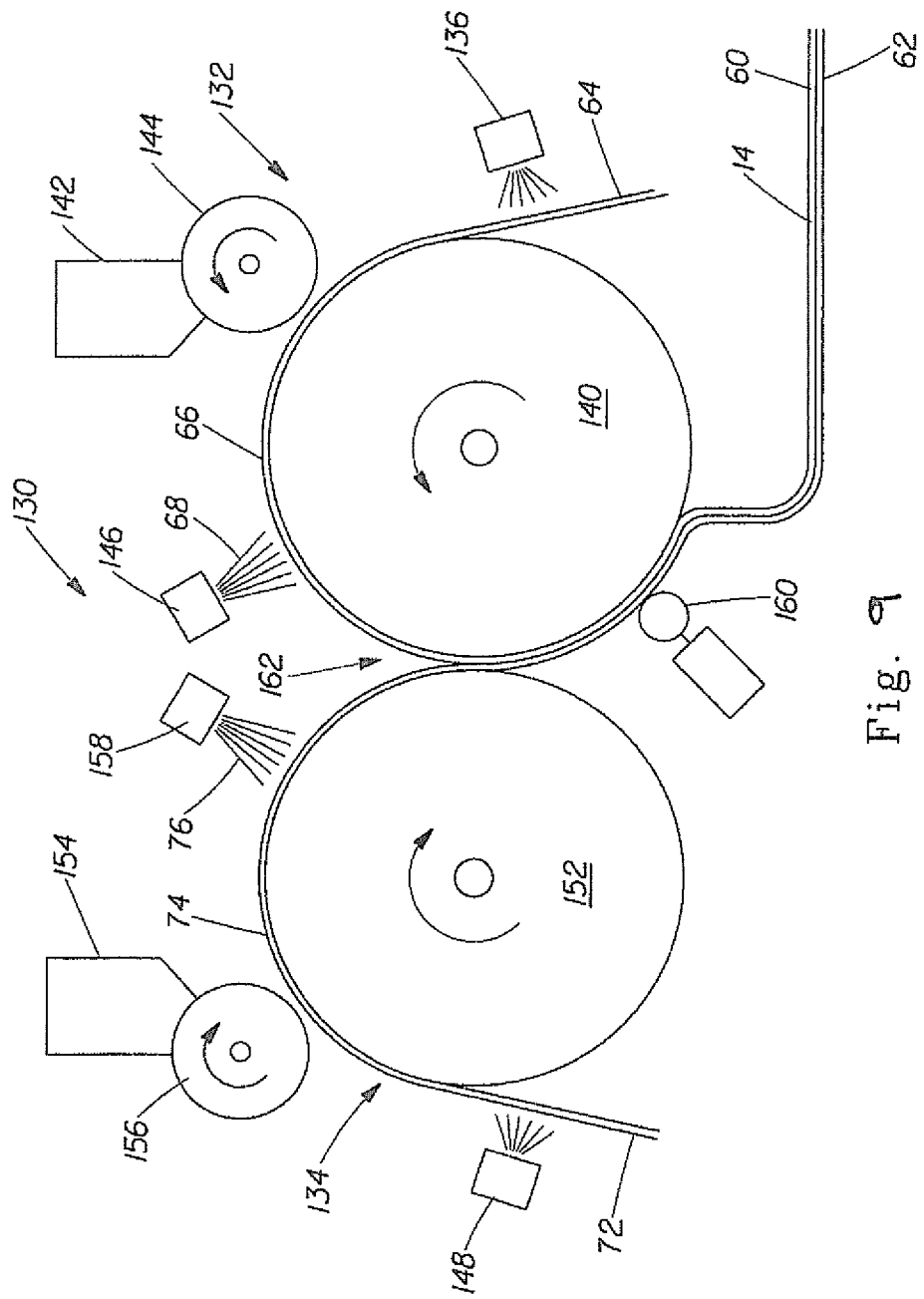
FIG. 9 is a schematic illustration of a process for making an absorbent core.

A printing system 130 for making an absorbent core 14 is shown in FIG. 9 and may include a first printing unit 132 for forming the first absorbent layer 60 of the absorbent core 14 and a second printing unit 134 for forming the second absorbent layer 62 of the absorbent core 14.

The first printing unit 132 may include a first auxiliary adhesive applicator 136 for applying an auxiliary adhesive to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic adhesive material applicator 146 for applying the thermoplastic adhesive material 68 to the substrate 64 and the absorbent particulate polymer 66 material thereon.

The second printing unit 134 may include a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 10:
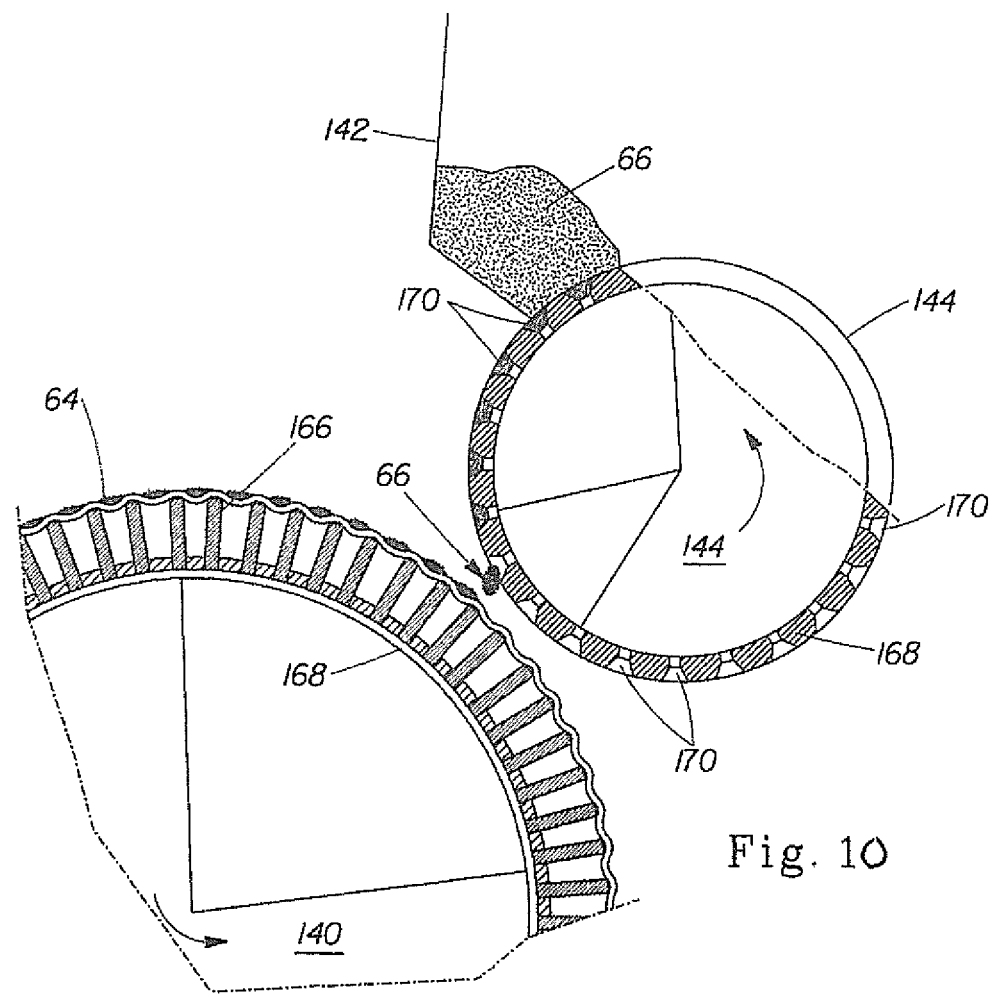
FIG. 10 is a partial sectional view of an apparatus for making an absorbent core.
Figure 13:
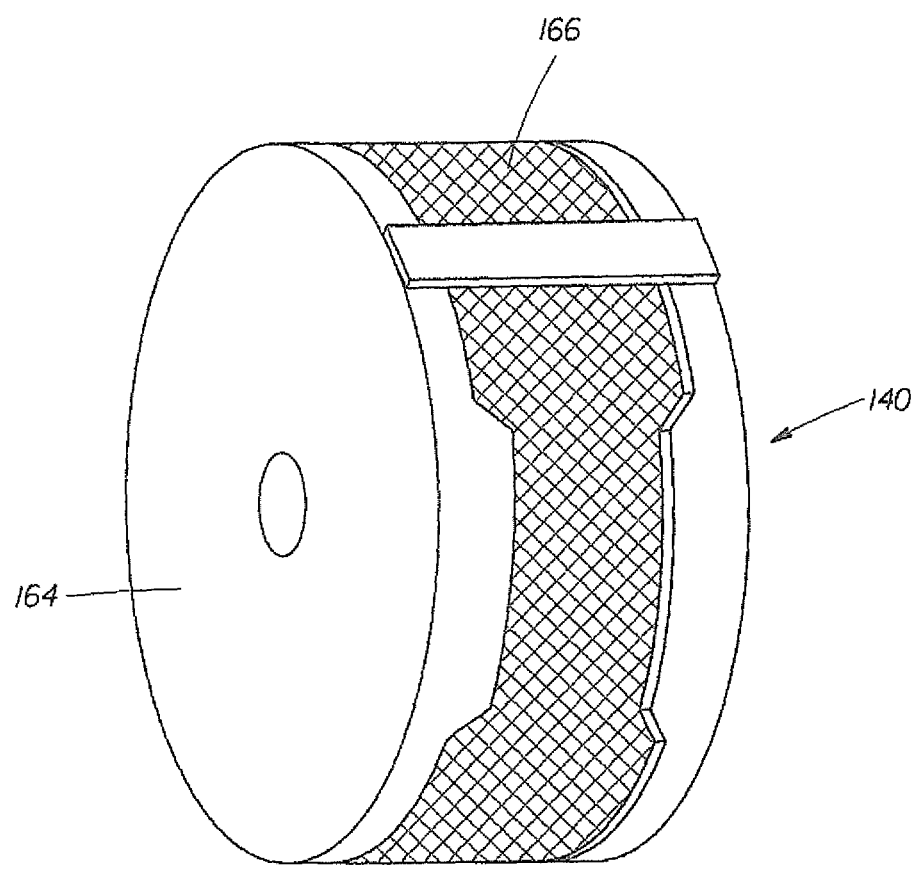
FIG. 13 is a perspective view of the supporting roll illustrated in FIG. 11.

Turning to FIG. 10, portions of the first hopper 142, first support roll 140, and first printing roll 144 are illustrated. As also shown in FIG. 13, the first rotatable support roll 140, which has the same structure as the second rotatable support roll 152, comprises a rotatable drum 164 and a peripheral vented support grid 166 for receiving the first substrate 64.

Figure 11:
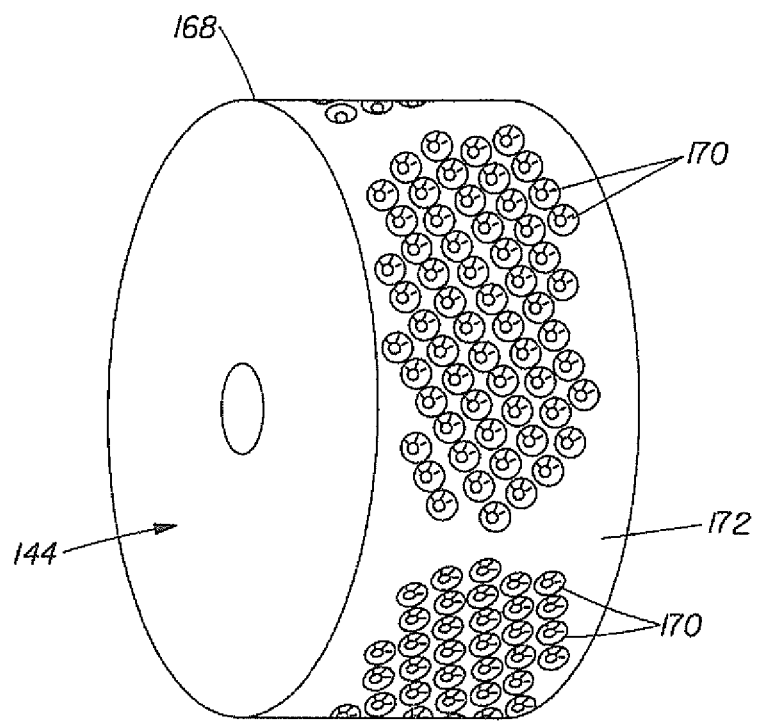
FIG. 11 is a perspective view of the printing roll illustrated in FIG. 10.
Figure 12:
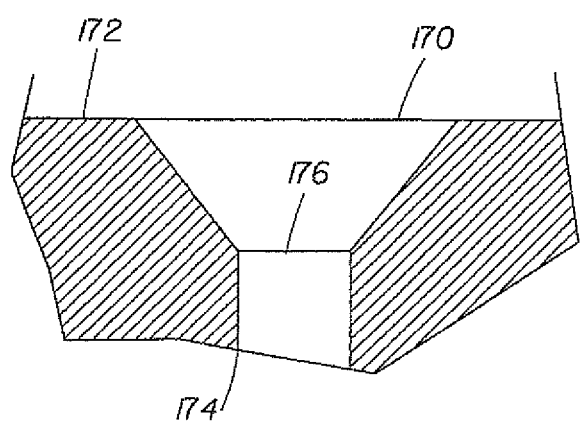
FIG. 12 is a partial sectional view of the printing roll illustrated in FIG. 11 showing an absorbent particulate polymer material reservoir.

As also shown in FIG. 11, the first printing roll 144, which has the same structure as the second printing roll 156, comprises a rotatable drum 168 and a plurality of absorbent particulate polymer material reservoirs 170 in a peripheral surface 172 of the drum 168. The reservoirs 170, such as shown in FIG. 12, may have a variety of shapes, including cylindrical, conical, or any other shape. The reservoirs 170 may lead to an air passage 174 in the drum 168 and include a vented cover 176 for holding adhesive particulate polymer material 66 in the reservoir and preventing the adhesive particulate polymer material 66 from falling or being pulled into the air passage 174.

Figure 5:
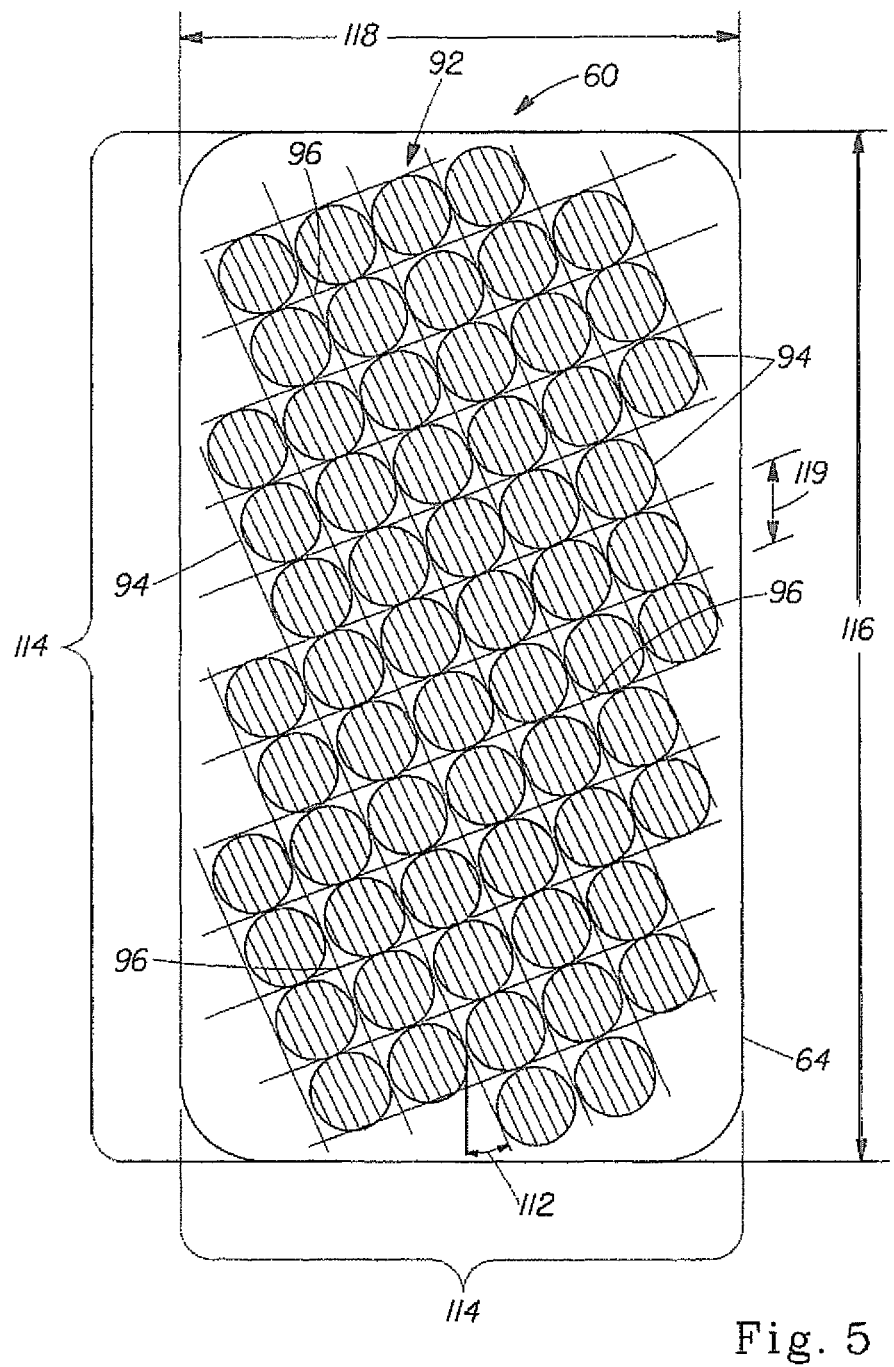
FIG. 5 is a plan view of the absorbent core layer illustrated in FIG. 3.
Figure 6:
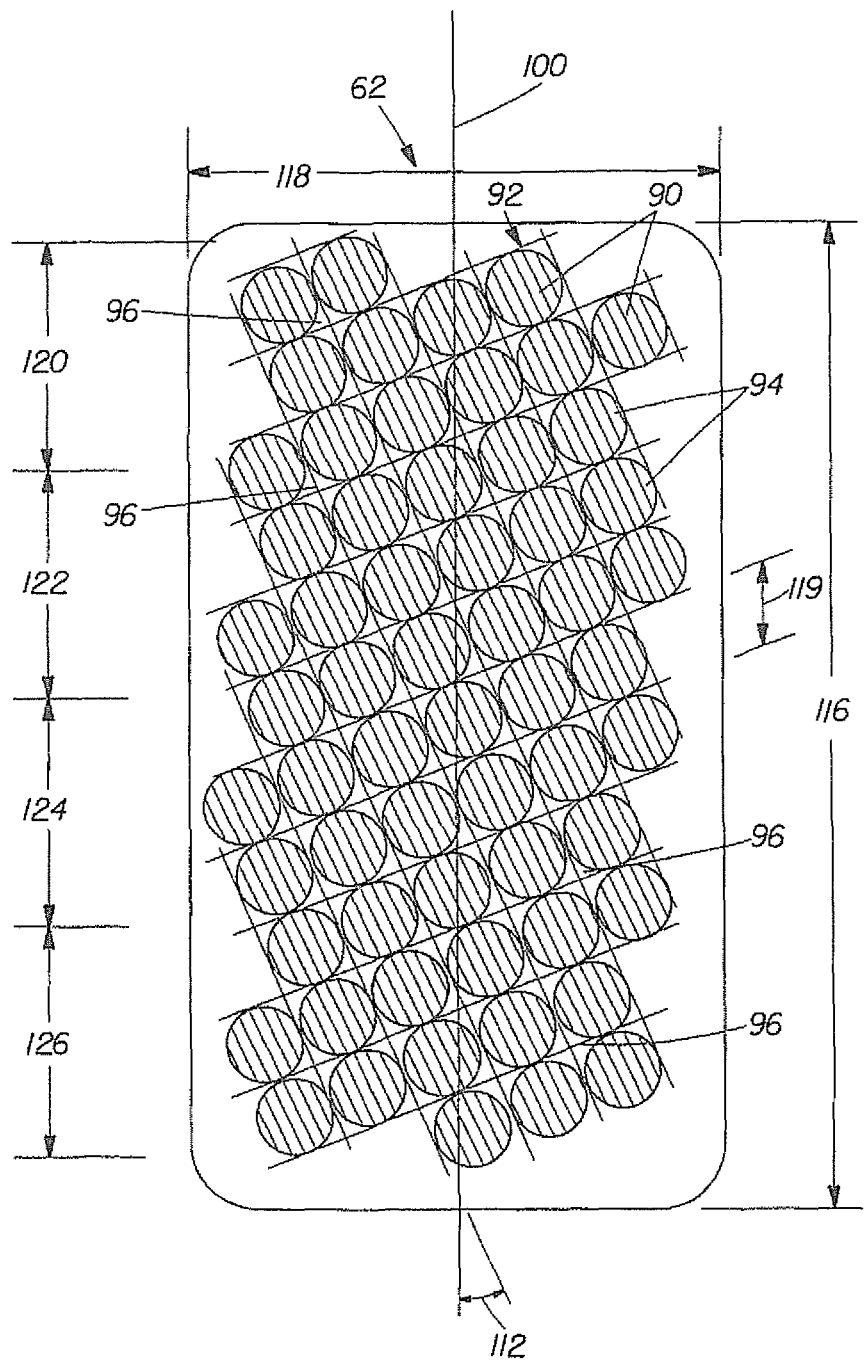
FIG. 6 is a plan view of a second absorbent core layer.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 such as shown in FIGS. 5 and 6. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In some configurations, a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

It is to be appreciated that various embodiments of diapers can be manufactured according the methods disclosed herein, such as for example, the absorbent articles disclosed in U.S. Patent Publication No. 2008/031621A1, which is hereby incorporated by reference herein.

Although much of the present discussion is presented in the context of absorbent articles in form of diapers, it is to be appreciated that absorbent articles, such as sanitary napkins can also be assembled according the methods and apparatuses disclosed herein. Absorbent articles, such as sanitary napkins may be designed to be worn in close proximity to the crotch of the wearer. Such absorbent articles need to provide for fluid acquisition and retention and may look aesthetically pleasing, as well as be comfortable to wear. Examples of sanitary napkins are provided in U.S. Patent Publication Nos. 2010/0036339; 2010/0036347; and 2010/0036349, the disclosures of which are herein incorporated by reference. In use, sanitary napkins are stressed by a variety of fluid handling demands. For instance, the central portion of the pad may be assaulted with fluid flow that may either be a trickle or a gush of fluid such as menstrual fluid. If the wearer is lying down on her front or back, fluid may have a tendency to run off of the front end or rear end of the absorbent article. Typical absorbent articles are approximately the same width as the crotch of the wearer, which can be somewhat narrow. Thus, there is potential for fluid to run off the sides of the absorbent article and soil the wings of the absorbent article, if present, or soil the wearer's undergarment and/or clothing.

A woman's crotch region can comprise many different types of tissues. For instance, the pubic area, labia majora, inner thigh, and anus can each have a different skin texture. Sanitary napkins commonly cover the labia, portions of the crotch forward of the labia, portions of the crotch rearward of the labia, and portions of the crotch laterally adjacent the labia. As a woman wearing a sanitary napkin moves, portions of the sanitary napkin can rub up against nearby body surfaces. Given the complex geometry of a woman's crotch region and the dynamic geometry of a woman's crotch as she moves, different portions of the woman's crotch are exposed to different rubbing forces and the friction between the sanitary napkin and wearer's crotch can vary depending on the location.

The moisture and chemical environments of a woman's crotch can also vary as a function of location. For instance, the labia majora may be exposed to menses and/or urine. The medial portion of the woman's pubic area may be exposed to perspiration. Portions adjacent the medial area may be subjected to more moisture due to the lack of hair and the tendency for a woman's panty to closely conform to the juncture of the inner thigh and the crotch and pubic area. The area near the anus may be exposed to more perspiration and anal leakage than areas further away from the anus.

Given the variety of fluid handling demands placed on different portions of an absorbent article, such as a sanitary napkin, the different physical interactions between portions of an absorbent article and portions of a wearer's body, and different moisture and chemical environments of different portions of a wearer's crotch region, there is continuing and unaddressed need for absorbent articles having aesthetically appealing, are comfortable to wear, but do not compromise the performance of the absorbent article. Sanitary napkins made with the embossing process described herein provide an aesthetically appealing surface to the body facing side of the article while not compromising the performance of the acquisition layer and maintaining the comfort of the article during wearing.

Figure 14:
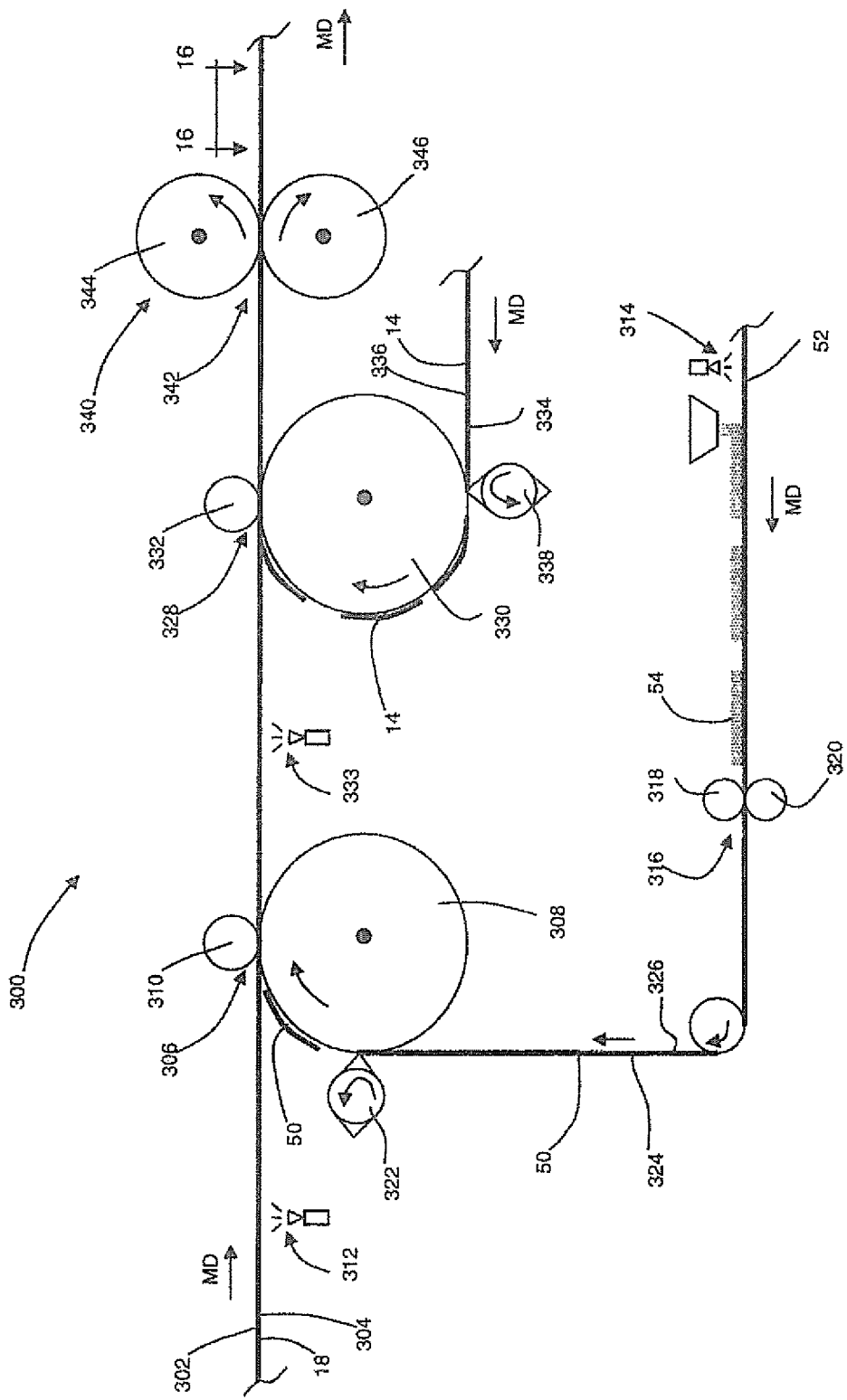
FIG. 14 is a schematic side view an apparatus for assembling components of an absorbent article and embossing a topsheet web.

As previously mentioned, the apparatuses and methods according to the present disclosure may be utilized to assemble various components of absorbent articles. For example, FIG. 14 shows a schematic view of a converting apparatus 300 adapted to manufacture diapers 10 having embossed topsheets 18. The method of operation of the converting apparatus 300 may described with reference to the various components of diapers 10 described above and shown in FIGS. 1-8. As described in more detail below, the converting apparatus 300 shown in FIG. 14 operates to advance a continuous topsheet web 18 in a machine direction. A liquid acquisition layer 50 and an absorbent core 14 are combined with the advancing topsheet web 18. The combined continuous topsheet web 18, liquid acquisition layer 50, and absorbent core 14 are then advanced through the embossing apparatus 340 to emboss a pattern in the continuous topsheet web 18.

As shown in FIG. 14, a continuous topsheet web 18 having a first surface 302 and an opposing second surface 304 is combined with a liquid acquisition system or layer 50. More particularly, the topsheet web 18 is advanced in a machine direction MD to a nip 306 defined between a carrier apparatus 308 and roll 310, where the topsheet web 18 and liquid acquisition layer 50 are combined. Before entering the nip 306, adhesive 312 may be applied to the second surface 304 of the topsheet web 18.

It is to be appreciated that the liquid acquisition layer 50 may be formed in various ways before being combined with the topsheet web 18. As discussed above, the liquid acquisition layer 50 may include one or more layers of material. For example, as shown in FIG. 14, the liquid acquisition layer 50 has a first surface 324 and an opposing second surface 326 and may include a first acquisition layer 52 and a second acquisition layer 54, wherein adhesive 314 is applied to the first acquisition layer 52 before being combined with the second acquisition layer 54. The liquid acquisition layer 50 may also advance through a nip 316 between rolls 318, 320 before advancing to the carrier apparatus 306. As shown in FIG. 14, the acquisition layer 50 may be cut into discrete lengths by a knife roll 322 on the carrier apparatus 308 before being combined with the topsheet web 18.

The carrier apparatus 308 and the knife roll 322 may utilize a cut and slip technique to space sequential discrete lengths of the acquisition layer 50 about the carrier apparatus 308. A cut and slip technique is an operation for achieving spacing between discrete components. An example operation for achieving spacing between discrete components is disclosed in U.S. Pat. No. 5,702,551, which is incorporated by reference herein. Other types of operations and equipment that may be used to cut and space discrete lengths of components are disclosed in U.S. Pat. Nos. 6,620,276; 6,811,019; and 7,587,966, which are incorporated by reference herein in their entireties. The discrete lengths of acquisition layer 50 are then combined with the topsheet web 18 at nip 306. In particular, the first surface 324 of the acquisition layer 50 may be adhered to the second surface 304 of the topsheet web 18 at nip 306. Although the acquisition layer 50 is shown in FIG. 14 as being cut into discrete lengths before being combined with the topsheet web 18, it is to be appreciated that in some embodiments a continuous length of acquisition layer 50 may be combined with the topsheet web 18.

From the nip 306, the combined topsheet web 18 and liquid acquisition layer 50 advance in the machine direction MD to a nip 328 defined between a carrier apparatus 330 and roll 332, where the topsheet web 18 and acquisition layer are combined with an absorbent core 14. Before entering the nip 328, adhesive 333 may be applied to the second surface 304 of the acquisition layer 50 and/or topsheet web 18.

It is to be appreciated that the absorbent core 14 may be formed in various ways before being combined with the topsheet web 18 and acquisition layer 50. For example, as shown in FIG. 14, the absorbent core 14 has a first surface 334 and an opposing second surface 336 and may be formed in accordance with the process description provided above with reference to FIGS. 9-13. As such, the absorbent core may include various components discussed above with reference to FIGS. 1-8, such as a first absorbent layer 60 and a second absorbent layer 62, wherein the first absorbent layer 60 of the absorbent core 14 may include a substrate 64, an absorbent particular polymer material 66 on the substrate 64, and a thermoplastic composition 68 on the absorbent particulate polymer material 66. And the second absorbent layer 62 of the absorbent core 14 may include a substrate 72, an absorbent particulate polymer material 74 on the second substrate 72, and a thermoplastic composition 66 on the absorbent particulate polymer material 74. As such, with reference to FIGS. 2 and 14, the substrate 72 may define the first surface 334 of the absorbent core 14, and the substrate 64 may define the second surface 336 of the absorbent core 14. As shown in FIG. 14, the absorbent core 14 may also be cut into discrete lengths by a knife roll 338 on the carrier apparatus 330 before being combined with the acquisition layer 50 and topsheet web 18.

The carrier apparatus 330 and the knife roll 338 may utilize a cut and slip technique to space sequential discrete lengths of the absorbent core 14 about the carrier apparatus 330. A cut and slip technique is an operation for achieving spacing between discrete components. An example operation for achieving spacing between discrete components is disclosed in U.S. Pat. No. 5,702,551, which is incorporated by reference herein. Other types of operations and equipment that may be used to cut and space discrete lengths of components are disclosed in U.S. Pat. Nos. 6,620,276; 6,811,019; and 7,587,966, which are incorporated by reference herein in their entireties. The discrete lengths of absorbent core 14 are then combined the acquisition layer 50 and topsheet web 18 at nip 328. In particular, the first surface 334 of the absorbent core 14 may be adhered to the second surface 326 of the acquisition layer 50 at nip 328. Although the absorbent core 14 is shown in FIG. 14 as being cut into discrete lengths before being combined with the acquisition layer 50 and topsheet web 18, it is to be appreciated that in some embodiments a continuous length of absorbent core 14 may be combined with the acquisition layer 50 and topsheet web 18.

From the nip 328, the combined topsheet web 18, acquisition layer 50, and absorbent core 14 advance in the machine direction MD to an embossing apparatus 340, where a pattern is embossed into the topsheet web 18. The embossing apparatus may include an embossing nip 342 defined between a patterned embossing roll 344 and an anvil roll 346. As shown in FIG. 14, the combined topsheet web 18, acquisition layer 50, and absorbent core 14 advance in the machine direction MD through the embossing nip 342 such that the outer surface of the patterned embossing roll 344 engages the first surface 302 of the topsheet web and the outer surface of the anvil roll engages the second surface 336 of the absorbent core 14. The topsheet web 18, acquisition layer 50, and absorbent core 14 are compressed while advancing through the embossing nip 342, and the embossing roll 344 embosses a pattern of embossments into the topsheet web 18. It is to be appreciated that the topsheet web 18, acquisition layer 50, and absorbent core 14 can be combined with other absorbent article components as described above in an assembly process, such as for example, a backsheet, fastening components, leg cuffs, and elasticated features.

It is to be appreciated that the embossing apparatus can be configured in various ways. In some embodiments, one or both the patterned embossing roll 344 and the anvil roll 346 may be heated. For example, in some embodiments, the patterned embossing roll 344 is heated to a surface temperature of 160° C. In some embodiments, the patterned embossing roll 344 and the anvil roll 346 have the same diameters and rotate at the same speeds. It should also be appreciated that the patterned embossing roll 344 and the anvil roll 346 may be made of various types of materials, wherein the patterned embossing roll 344 and the anvil roll 346 are made from the same or different types of materials. For example, in some embodiments, both the patterned embossing roll 344 and the anvil roll 346 are made from D2 tool steel. In addition, the embossing apparatus may be configured such that the patterned embossing roll includes an embossing pattern on the outer surface and the anvil roll includes a smooth outer surface.

It is to be appreciated that the embossing apparatus can be configured to emboss various types of patterns in the topsheet 18. As such, the outer surface of the patterned embossing roll 344 can be configured with various types of embossing elements (or protrusions) in the form of nubs and/or ridges that compress and/or deform the topsheet 18 and other components passing through the embossing nip 342.

As used herein, the term "discrete" with reference to embossing elements means that the embossing element (which may be interchangeably refereed to herein as an embossing protrusion or protuberance) is not contiguous with another embossing element, but rather is separated from all other embossing elements by some distance. Although discrete embossing elements can be any size or shape, in some embodiments, the embossing elements are circular or oval in cross-section at their distal end (i.e. the end farthest away from the surface from which the embossing element extends). If generally circular in cross-section, the discrete embossing elements may have a diameter at their distal end of less than about 15 mm, less than about 7.5 mm, less than about 5.0 mm, less than about 3.0 mm, less than about 1.0 mm, between about 1.0 mm and about 15 mm, or any number within this range. In embodiments wherein the discrete embossing elements are non-circular, the discrete embossing elements may have a major length dimension (i.e. the longest dimension at the distal end parallel to the surface from which the embossing element extends) and a minor length dimension (i.e. the shortest dimension at the distal end parallel to the surface from which the embossing element extends). The dimensions set forth above with regard to the diameter of the distal end of generally circular discrete embossing elements are applicable to the major length at the distal end of non-circular discrete embossing elements. Further, in such cases, in order to not be considered linear, the discrete embossing elements will have a ratio of the major length to the minor length dimension of less than about 3.5:1, less than about 3:1, less than about 2.5:1, between about 3.5:1 and about 1:1, or any ratio within the range.

Figure 15:
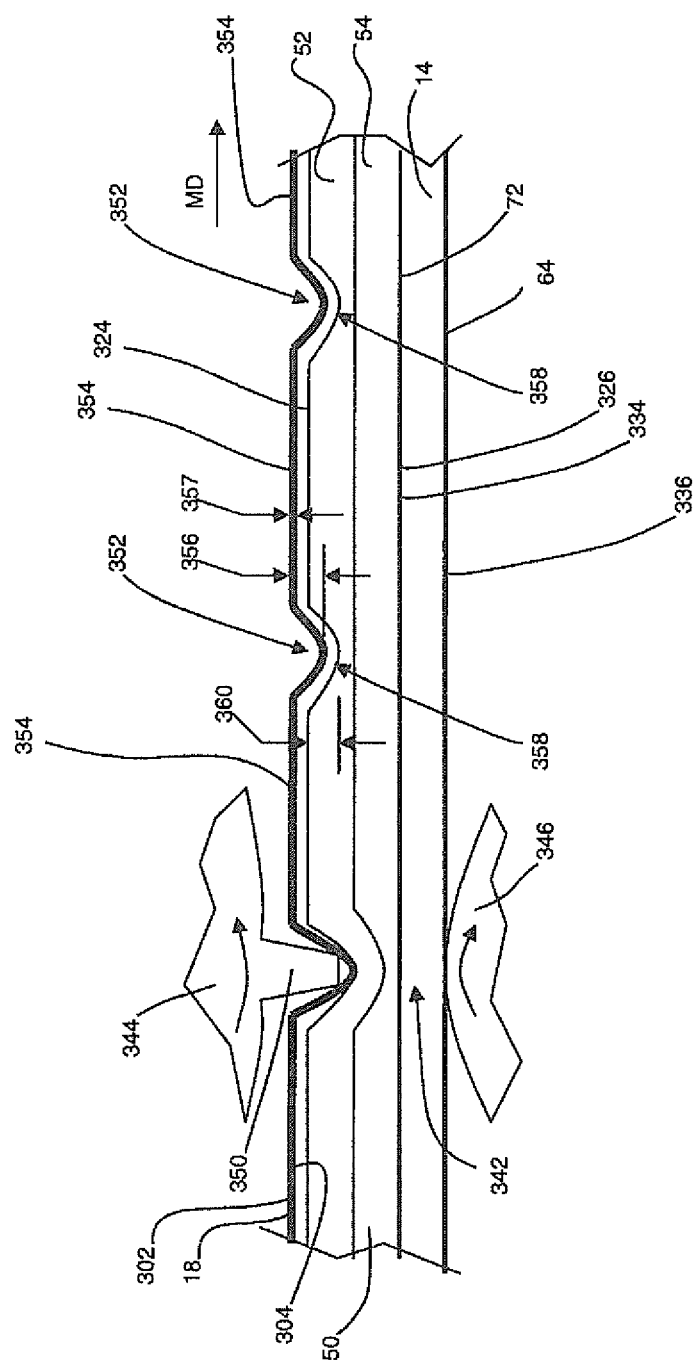
FIG. 15 is a detailed cross-sectional view of a topsheet web, acquisition layer, and absorbent core advancing through an embossing nip.

Embossing elements act on a substrate to create correspondingly shaped embossments in the substrate. As used herein, the term "discrete" with reference to embossments means that the embossment (which may be interchangeably referred to herein as an indented region) is not contiguous with another embossment, but rather is separated from all other embossments by some distance. As shown in FIGS. 15 and 16, for example, discrete embossments (indented regions) 352 are separated from each other by unembossed regions (unindented regions) 354.

In some embodiments, the embossing elements may include an average height of about 7000 μm. Other embodiments may have embossing elements having heights greater than about 3000 μm, for example, greater than about 2000 μm, greater than about 1000 μm or any individual number within this range.

As used herein, the term "continuous" refers to an embossing pattern including an embossing element that extends continuously along at least one path without a break or interruption. That is, one can trace along the entirety of the continuous embossing pattern without ever having to cross a break or interruption in the pattern.

As used herein, the term "linear" as it refers to embossing elements means that embossing elements that have a length and a width, wherein the ratio of the length to the width is as least about 4:1, at least about 5:1 or at least about 10:1. Further, a linear element could be continuous, as described herein. Thus, the length would generally correspond to the length of the centerline of the outline of the shape formed by the linear embossing elements as opposed to a distance bisecting or otherwise cutting across a portion of the shape. In certain embodiments, it may be desirable that the width of the linear embossing element be less than about 15.0 mm, less than about 7.5 mm, less than about 5.0 mm, less than about 2.5 mm, less than about 1.0 mm, between about 1.0 mm and about 15.0 mm, or any number within this range.

The term linear does not require that the embossing element be of any particular shape, other than set forth herein, and it is contemplated that such linear embossing elements can include generally straight lines or curved lines or combinations thereof. In addition, a "linear" element need not be uniform in width and/or height. (For the purposes of this application, the width measurement used to determine the length to width ratio is the widest (or largest width measurement) taken along the length of the embossing element.) Further, the linear embossing elements can form patterns and/or shapes that repeat or do not repeat. Thus, the pattern, if any, formed by the linear embossing elements can be regular or non-regular, as desired.

The pattern could include linear embossing elements in addition to the discrete and/or non-discrete embossing elements. More specifically, the linear embossing elements may have a length L to width W ratio that is as least about 4:1, at least about 5:1 or at least about 10:1. Although the length L and width W of the linear embossing elements can be any suitable number, in certain embodiments, it may be desirable that the width W of the linear embossing element be less than about 15 mm, less than about 7.5 mm, less than about 5.0 mm, less than about 2.5 mm, less than about 1.0 mm, between about 1.0 mm and about 15 mm, or any number within this range.

As noted above, the term linear does not require that the embossing element be of any particular shape and it is contemplated that such linear embossing elements can include generally straight lines or curved lines or combinations thereof. Also, as stated above, linear element need not be uniform in width W. A few non-limiting examples of various different possible linear embossing elements with non-uniform widths are also possible.

The linear embossing elements can form patterns and/or shapes that repeat or do not repeat. The linear embossing elements may be shaped such that they include an enclosed or at least partially enclosed region. It may also be desirable to design the discrete embossing elements such that the total area of the area of the distal ends of all of the discrete embossing elements is less than about 25%, less than about 20%, less than about 15%, less than about 13%, less than about 12.5%, less than about 10%, less than about 5% or even less than about 2.5% of the total planar projected area defined by the smallest rectangle that can surround the combined embossing pattern for a single absorbent article.

The combined embossing pattern can include a repeating pattern of embossing elements (e.g. linear and/or discrete). The combined embossing pattern can be repeated from absorbent article to absorbent article on a production line.

To calculate a total area value for the distal ends of any particular type of embossing element or elements the individual area of each of the distal ends, is measured. The total area value is the sum of the individual areas measured. One suitable method for obtaining the area measurements is by using computer aided drafting software, such as AUTOCAD 2004.

It may be desirable that the total area of the distal ends of the embossing element (e.g. linear and/or discrete) in any combined embossing pattern is a certain area or less. For example, it may be desirable that the total area of the distal ends of the linear embossing elements is less than about 10 cm2, less than about 7.5 cm2, less than about 5.0 cm2, less than about 3.0 cm2 or less than about 2.5 cm2.

As shown in FIG. 15, the resulting embossed topsheet 18 may have embossments (indentations) 352 with various average embossment depths 356. For example, in some embodiments, the average embossment depth 356 may be at least about 650 µm. Other embodiments may have embossments 352 with embossment depths 356 greater than 1000 µm, greater than about 1250 µm, greater than about 1450 µm, at least about 1550 µm, at least about 1800 µm, at least about 2000 µm, at least about 3000 µm, at least about 4000 µm, between about 650 µm and about 4000 µm or any individual number within this range. The average embossment depth may be measured by the Embossment Depth Test Method using a GFM MikroCAD optical profiler instrument, as described in the nonprovisional U.S. patent application Ser. No. 13/047,133 entitled, "Disposable Absorbent Articles with an Embossed Topsheet," filed on Mar. 14, 2011, which is incorporated by reference herein.

With continued reference to FIG. 15, the embossing apparatus may also be configured to operate with various different nip pressures and embossment depths that may result in compression of different components while passing through the embossing nip 342. Depending on the absorbent core construction, it may also be desirable to avoid tearing or otherwise rupturing the substrate 72 and/or substrate 64 of the absorbent core 14 while passing through the embossing nip 342. The embossing apparatus may also be configured to avoid tearing or otherwise rupturing the topsheet 18.

In some embodiments as the topsheet web 18, acquisition layer 50, and absorbent core 14 advance through the embossing nip 342, the topsheet 18 and the acquisition layer 50 are deformed by the embossing elements 350 on the patterned embossing roll 344, while the absorbent core 14 is not deformed by the embossing elements 350. For example, as shown in FIG. 15, as the topsheet web 18, acquisition layer 50, and absorbent core 14 advance through the embossing nip 342, the topsheet 18, first acquisition layer 52, and second acquisition layer 54 are deformed by the embossing elements 350 on the patterned embossing roll 344, while the absorbent core 14 is not deformed by the embossing elements. In some embodiments, as the topsheet web 18, acquisition layer 50, and absorbent core 14 advance through the embossing nip 342, the topsheet 18 and the first acquisition layer 52 are deformed by the embossing pattern on the patterned embossing roll 344, while the absorbent core 14 and the second acquisition layer 54 are not deformed by the embossing pattern. In still other embodiments, the topsheet web 18, acquisition layer 50, and absorbent core 14 are all deformed by the embossing pattern while advancing through the embossing nip 342.

As previously mentioned, the embossing apparatus may be configured to avoid tearing or otherwise rupturing components passing through the embossing nip 342. In some embodiments, the embossing apparatus may be configured to avoid the exerting pressures on the components that may result in thermally bonding fibers of various components, such as for example, fibers of a nonwoven topsheet web 18. It should also be appreciated that various components may not be permanently deformed and/or compressed after passing through the embossing nip 342. For example, as shown in FIG. 15, the topsheet 18, first acquisition layer 52, and second acquisition layer are all deformed and/or compressed while passing through the embossing nip 342. However, the degree of compression in the topsheet 18 and first acquisition layer 52 is lessened after advancing from the embossing nip 342, while the compression of the second acquisition layer 54 is substantially entirely removed.

In some embodiments after advancing from the embossing nip 342, such as shown in FIGS. 15 and 16, the topsheet 18 includes discrete embossments (discrete indentations) 352 having a depth 356. The depth 356 of the embossments 352 in the topsheet 18 may be greater than the caliper 357 of the topsheet 18. The first acquisition layer 52 may also include embossments 358 having a depth 360. The depth 360 of the embossments 358 in the first acquisition layer 52 may be the same as or less than the depth 356 of the embossments 352 in the topsheet 18. In embodiments where the topsheet 18 and liquid acquisition layer 50 pass through the embossing nip 342 at the same time, the embossments 358 in the first acquisition layer 52 may have corresponding locations, shapes, and/or sizes with the embossments 352 in the topsheet 18.

It is to be appreciated that combined embossed topsheet 18, liquid acquisition layer 50, and absorbent core 14 may be combined with other components, such as for example, backsheet webs, leg cuffs, ears, side, panels, leg cuffs, and/or fastening elements, to produce an absorbent article such as described above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for assembling disposable absorbent articles, each absorbent article comprising a chassis having a first waist region longitudinally opposed to a second waist region, and having a longitudinal axis and a lateral axis, the chassis comprising: a topsheet, a backsheet, and a liquid acquisition layer and a substantially cellulose free absorbent core disposed between the topsheet and the backsheet, the process comprising the steps of:

advancing a continuous topsheet web having a first surface and an opposing second surface in a machine direction;

combining a liquid acquisition layer with the continuous topsheet web, wherein the liquid acquisition layer includes a first surface and an opposing second surface, and wherein the first surface of the liquid acquisition layer is positioned in a facing relationship with the second surface of the continuous topsheet web, wherein the liquid acquisition layer comprises an upper acquisition layer and a lower acquisition layer;

combining an absorbent core with the liquid acquisition layer, wherein the absorbent core includes a first surface and an opposing second surface, and wherein the first surface of the absorbent core is positioned in a facing relationship with the second surface of the liquid acquisition layer;

providing an embossing nip between a rotating patterned embossing roll and a rotating anvil roll; and embossing a pattern in the continuous topsheet web and upper acquisition layer without bonding the continuous topsheet web and the upper acquisition layer together and without embossing the lower acquisition layer and the absorbent core by advancing the combined continuous topsheet web, liquid acquisition layer, and absorbent core through the embossing nip, wherein the rotating patterned embossing roll contacts the first surface of the continuous topsheet web, and wherein the rotating anvil roll contacts the second surface of the absorbent core.

2. The process of claim 1, wherein the step of combining a liquid acquisition layer with the continuous topsheet web further comprises the operation of applying adhesive to the second surface of the continuous topsheet web.

3. The process of claim 1, wherein the step of combining an absorbent core with the liquid acquisition layer further comprises the operation of applying adhesive to the second surface of the liquid acquisition layer.

4. The process of claim 1, wherein the upper acquisition layer defines the first surface of the liquid acquisition layer and the lower acquisition layer defines the second surface of the liquid acquisition layer.

5. The process of claim 1, further comprising the step of: combining a continuous backsheet web with the combined continuous topsheet web, liquid acquisition layer, and absorbent core exit the embossing nip.

6. The process of claim 1, further comprising the step of heating the patterned embossing roll.

7. A process for assembling disposable absorbent articles, each absorbent article comprising a chassis having a first waist region longitudinally opposed to a second waist region, and having a longitudinal axis and a lateral axis, the chassis comprising: a topsheet, a backsheet, and a liquid acquisition layer and a substantially cellulose free absorbent core disposed between the topsheet and the backsheet, the process comprising the steps of:

advancing a continuous topsheet web having a first surface and an opposing second surface in a machine direction;

combining a liquid acquisition layer with the continuous topsheet web, wherein the liquid acquisition layer includes a first surface and an opposing second surface, and wherein the first surface of the liquid acquisition layer is positioned in a facing relationship with the second surface of the continuous topsheet web, wherein the liquid acquisition layer comprises an upper acquisition layer and a lower acquisition layer;

combining an absorbent core with the liquid acquisition layer, wherein the absorbent core includes a first surface and an opposing second surface, and wherein the first surface of the absorbent core is positioned in a facing relationship with the second surface of the liquid acquisition layer;

providing an embossing nip between a rotating embossing roll and a rotating anvil roll, the embossing roll comprising an embossing element; and creating indented regions in the continuous topsheet web and the upper acquisition layer without bonding the continuous topsheet web and the upper acquisition layer together without creating indented regions in the lower acquisition layer and the absorbent core by advancing the combined continuous topsheet web, liquid acquisition layer, and absorbent core through the embossing nip, wherein the embossing element contacts the first surface of the continuous topsheet web, and wherein the rotating anvil roll contacts the second surface of the absorbent core.

8. The process of claim 7, wherein the step of combining a liquid acquisition layer with the continuous topsheet web further comprises the operation of applying adhesive to the second surface of the continuous topsheet web.

9. The process of claim 7, wherein the step of combining an absorbent core with the liquid acquisition layer further comprises the operation of applying adhesive to the second surface of the liquid acquisition layer.

10. The process of claim 7, wherein the upper acquisition layer defines the first surface of the liquid acquisition layer and the lower acquisition layer defines the second surface of the liquid acquisition layer.

11. The process of claim 7, further comprising the step of: combining a continuous backsheet web with the after the combined continuous topsheet web, liquid acquisition layer, and absorbent core exit the embossing nip.

12. The process of claim 7, further comprising the step of heating the embossing roll.

* * * * *